US009446265B2

(12) United States Patent
Jansen et al.

(10) Patent No.: US 9,446,265 B2
(45) Date of Patent: *Sep. 20, 2016

(54) COSMETIC COMPOSITION

(71) Applicant: The Procter & Gamble Company, Cincinnati, OH (US)

(72) Inventors: Joseph Harry Jansen, Harrison, OH (US); Joseph Michael Zukowski, Cincinnati, OH (US); Paul Robert Tanner, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/245,230

(22) Filed: Apr. 4, 2014

(65) Prior Publication Data

US 2015/0196463 A1    Jul. 16, 2015

Related U.S. Application Data

(60) Provisional application No. 61/927,231, filed on Jan. 14, 2014, provisional application No. 61/927,236, filed on Jan. 14, 2014, provisional application No. 61/927,244, filed on Jan. 14, 2014, provisional application No. 61/927,255, filed on Jan. 14, 2014.

(51) Int. Cl.
| | |
|---|---|
| *A61Q 1/12* | (2006.01) |
| *A61K 8/891* | (2006.01) |
| *A61K 8/73* | (2006.01) |
| *A61Q 1/02* | (2006.01) |
| *A61Q 1/00* | (2006.01) |
| *A61K 8/895* | (2006.01) |
| *A61K 8/02* | (2006.01) |
| *A61K 8/06* | (2006.01) |
| *A61Q 19/00* | (2006.01) |

(52) U.S. Cl.
CPC ............... *A61Q 1/12* (2013.01); *A61K 8/025* (2013.01); *A61K 8/062* (2013.01); *A61K 8/732* (2013.01); *A61K 8/891* (2013.01); *A61K 8/895* (2013.01); *A61Q 1/00* (2013.01); *A61Q 1/02* (2013.01); *A61Q 19/00* (2013.01); *A61K 2800/412* (2013.01)

(58) Field of Classification Search
CPC ...... A61K 8/891; A61K 8/732; A61K 8/895; A61K 8/025; A61K 8/062; A61K 2800/412; A61Q 1/02; A61Q 1/12; A61Q 19/00; A61Q 1/00
USPC ........................................... 424/401, 63, 69
See application file for complete search history.

(56) References Cited

U.S. PATENT DOCUMENTS

| | | | |
|---|---|---|---|
| 3,755,560 A | 8/1973 | Dickert | |
| 4,421,769 A | 12/1983 | Dixon | |
| 5,223,559 A * | 6/1993 | Arraudeau | ............ A61K 8/025 |
| | | | 424/401 |
| 5,871,791 A | 2/1999 | Noble | |
| 6,367,484 B1 | 4/2002 | Ramin | |
| 6,531,116 B1 | 3/2003 | Utecht | |
| 6,780,422 B2 * | 8/2004 | Brieva et al. | ................. 424/401 |
| 6,872,401 B2 | 3/2005 | Seyler | |
| 2002/0193513 A1 | 12/2002 | Bara | |
| 2003/0031642 A1 | 2/2003 | Lezer | |
| 2003/0049212 A1 | 3/2003 | Robinson | |
| 2003/0095941 A1 | 5/2003 | Anderson | |
| 2004/0086473 A1 | 5/2004 | Rabe | |
| 2004/0086474 A1 | 5/2004 | Rabe | |
| 2004/0228819 A1 | 11/2004 | Rabe | |
| 2005/0058677 A1 | 3/2005 | Ricard | |
| 2005/0058678 A1 | 3/2005 | Ricard | |
| 2006/0057127 A1 | 3/2006 | Liu | |
| 2006/0257346 A1 | 11/2006 | Mohammadi | |
| 2007/0224141 A1 | 9/2007 | Themens | |
| 2007/0237730 A1 | 10/2007 | Polonka | |
| 2008/0145435 A1 | 6/2008 | Ricard | |
| 2008/0181956 A1 | 7/2008 | Ha | |
| 2009/0148393 A1 | 6/2009 | Maitra | |
| 2009/0208443 A1 | 8/2009 | Polonka | |
| 2010/0266651 A1 * | 10/2010 | Czech | .................... A61K 8/893 |
| | | | 424/401 |
| 2010/0322983 A1 | 12/2010 | Griffiths-Brophy | |
| 2014/0341823 A1 | 11/2014 | Alard | |

FOREIGN PATENT DOCUMENTS

| | | |
|---|---|---|
| DE | 10157490 | 6/2003 |
| EP | 0502769 A1 | 9/1992 |
| EP | 1513491 B1 | 3/2005 |
| EP | 1767191 A1 | 3/2007 |
| EP | 2382961 A2 | 11/2011 |
| EP | 1902704 B1 | 11/2013 |

(Continued)

OTHER PUBLICATIONS

English Translation of EP 2 382 296 A2, published Nov. 2, 2011.*
U.S. Appl. No. 14/596,360, filed Jan. 14, 2015, Joseph Harry Jansen.
U.S. Appl. No. 14/596,363, filed Jan. 14, 2015, Joseph Harry Jansen.
U.S. Appl. No. 14/596,374, filed Jan. 14, 2015, Joseph Harry Jansen.

(Continued)

*Primary Examiner* — Blessing M Fubara
(74) *Attorney, Agent, or Firm* — John G. Powell

(57) ABSTRACT

A finisher composition that provides improved look and feel benefits to an underlying skin care product. The finisher composition is an oil-in-water emulsion that includes from 10 to 25 wt % of substantially spherical starch particles having a mean particle size of from 5 to 30 microns. The oil phase of the finisher includes a non-volatile oil present at an amount to provide a weight ratio of non-volatile oil to starch particles of from 1:10 to 3:2. The aqueous phase of the finisher includes from 20 to 85 wt % of water.

12 Claims, No Drawings

(56) References Cited

FOREIGN PATENT DOCUMENTS

| FR | 2903306 | 6/2012 |
|---|---|---|
| FR | 2964562 B1 | 8/2012 |
| GB | 2423250 | 8/2006 |
| JP | 2003300831 | 10/2003 |
| WO | WO02/092047 | 11/2002 |
| WO | WO2013/088046 | 6/2013 |
| WO | WO2013/169506 A2 | 11/2013 |
| WO | WO2013/166342 A3 | 10/2014 |

OTHER PUBLICATIONS

U.S. Appl. No. 14/596,379, filed Jan. 14, 2015, Joseph Harry Jansen.
U.S. Appl. No. 14/245,241, filed Apr. 4, 2014, Joseph Harry Jansen.
U.S. Appl. No. 14/445,434, filed Jul. 29, 2014, Joseph Harry Jansen.
U.S. Appl. No. 14/445,456, filed Jul. 29, 2014, Joseph Harry Jansen.
"The CIE 1976 Color Difference Formulas," *Color Research Applications*, vol. 2, pp. 7-11 (1977).
Todd, Charles, et al. "Volatile Silicone Fluids for Cosmetics", vol. 91 Cosmetics and Toiletries pp. 27-32 (Jan. 1976).
"Prime & Anti-Shine Balm" GNPD Nov. 1, 2013; Record ID 2247832.
International Search Report PCT/US2015/011366; Mailing Date Apr. 30, 2015; 22 pages.
International Search Report PCT/US2015/011367; Mailing Date Apr. 30, 2015; 22 pages.
International Search Report PCT/US2015/011370; Mailing Date Apr. 30, 2015; 21 pages.
International Search Report PCT/US2015/011372; Mailing Date Apr. 30, 2015; 22 pages.
International Search Report PCT/US2015/011373; Mailing Date Apr. 14, 2015; 10 pages.
International Search Report PCT/US2015/011374; Apr. 17, 2015; 11 pages.

\* cited by examiner

COSMETIC COMPOSITION

FIELD OF THE INVENTION

The present disclosure relates to a cosmetic composition that helps improve the appearance and feel of human skin. More specifically, the cosmetic composition is a finisher composition that is applied as an overlying top layer to an underlying layer of skin care composition, thereby improving the look and feel of the treated skin.

BACKGROUND OF THE INVENTION

Personal care products are well known and widely used. These products have long been employed to cleanse and moisturize, deliver actives, hide imperfections and to reduce the oiliness and shine on keratinous surfaces. Personal care products have also been used to alter the color and appearance of skin and hair. A variety of personal-care compositions are available to provide skin care benefits and to counteract what many consider undesirable "signs of skin aging," such as fine lines, wrinkles, and uneven skin texture. Of these benefits, the look and feel of human skin are arguably the two most important and desired effects by consumers.

Many products are designed to improve the look of human skin and many products are directed to improving the feel. Traditionally, a wide variety of different functional materials are combined in a single skin care product in an attempt to deliver a range of benefits to consumers. For example, a typical skin care product might contain: humectants and other skin actives to improve the condition and health of the skin; emollients to lubricate the skin; and a wide variety of powders to provide a skin feel and immediate skin appearance benefit.

Humectants are well known in the skin care industry, and may be incorporated into a personal care composition to provide a multitude of skin health and appearance benefits, such as increasing skin translucency (e.g., by less surface scattering and reducing refractive index gradients in the stratum corneum), reducing visible texture (e.g., by plumping of the stratum corneum) and generally better functioning and stronger skin. Glycerin is a commonly known humectant used widely in the field of cosmetics. It is not uncommon for Glycerin to be incorporated into skin care compositions at relatively high levels to maximize the skin health benefit it provides. But glycerin is a relatively thick, sticky material and high levels of glycerin can feel undesirably sticky and heavy on the skin. Moreover, high levels of glycerin on the skin can make it look undesirably shiny and greasy, at least in part because glycerin is slow to absorb into the skin.

In some instances, particulate materials may be added to a personal care composition to address the undesirable skin feel and look properties imparted by one or more ingredients in the composition, such as glycerin. For example, micronized or spherical polymer particles may be used to provide feel, visible texture and/or wrinkle reduction benefits. Such particulate materials may provide an immediate visible texture (e.g., lines and wrinkles, pores, bumpy surface) reduction benefit to the skin by diffusely reflecting light, thereby providing a matting effect to the skin. In another example, particles may be added to a conventional skin care product to address the undesirable feel properties of a component ingredient such as glycerin (e.g., reduce the tacky feel). However, there are tradeoffs when attempting to increase these feel and look benefits. In some instances, the relatively high levels of powder required to provide the desired benefit may lead to products that are hard to spread on skin and/or products become noticeably white and can flake off the skin. In some instances, even incorporating relatively high amounts of powder may still fail to provide a suitable reduction in undesirable feel properties such as tackiness. Further, some particulate materials may act as an opacifying agent, which can turn the consumer product into make-up or make-up like product. While opacifying agents can provide a color benefit to a target skin surface, opacifying agents can also cause an increase in the visible texture of the skin, thus making undesirable textural features of the skin (e.g., wrinkles, pores, bumpy surface) more visible rather than hiding them.

Therefore, a need exists for a personal care composition that provides improved look and feel characteristics when used in conjunction with a conventional skin care composition. In particular, there remains a need for a personal care composition that improves the undesirable look and feel properties of a conventional skin care composition when applied as an overlying layer to one or more underlying base layer(s) of skin care compositions, which contain high levels of ingredients with undesirable feel and look properties, such as humectants. There is also a need for a personal care composition that provides improved look and feel characteristics when used in conjunction with a conventional skin care composition and includes little or no pigments or colorants.

SUMMARY OF THE INVENTION

In order to provide a solution to the problems above, disclosed herein is a finisher composition comprising: from about 10 to 25 wt % of substantially spherical starch particles having a mean particle size of from about 5 to 30 microns; a non-volatile oil, wherein a weight ratio of non-volatile oil to starch particles is from about 1:10 to about 3:2; from about 20 to 85 wt % of water; and, optionally, from about 1 to 20 wt % of a volatile oil. The composition is an oil-in-water emulsion, and the composition is substantially free of humectant.

Also disclosed is a finisher composition, comprising: from about 10 to 25 wt % of substantially spherical starch particles having a mean particle size of from about 5 to 30 microns; a non-volatile oil, wherein a weight ratio of non-volatile oil to starch particles is from about 1:10 to about 3:2; and from about 20 to 85 wt % of water. The composition also includes less than 1 wt % of a pigment and has a contrast ratio of less than about 20 according to the Contrast Ratio Test.

Further disclosed is a finisher composition, comprising: from about 10 to 25 wt % of substantially spherical starch particles having a mean particle size of from about 5 to 30 microns; a non-volatile oil comprising at least about 70% of a non-volatile silicone, wherein a weight ratio of non-volatile oil to starch particles is from about 1:10 to about 3:2; and from about 20 to 85 wt % of water, wherein the composition has a contrast ratio of less than about 20 according to the Contrast Ratio method.

DETAILED DESCRIPTION

Percentages are by weight of the composition or the particular phase being described, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at ambient conditions, where "ambient conditions" means conditions at about 25° C., under about one atmosphere of pressure, and at about 50% relative humidity.

Definitions

"Apply" or "application," as used in reference to a composition, means to apply or spread the composition onto a keratinous tissue surface.

"Derivative" refers to a molecule similar to that of another one, but differing from it in respect of a certain functional moiety. Derivatives may be formed by known reactive pathways. Suitable functional moieties include esters, ethers, amides, amines, carboxylic acids, hydroxyls, halogens, thiols, and/or salt derivatives of the relevant molecule.

"Keratinous tissue" refers to keratin-containing layers disposed as the outermost protective covering of mammals which includes, but is not limited to, skin, hair, nails, cuticles, etc.

"Non-volatile" means a material that exhibit a vapor pressure of no more than about 0.2 mm Hg at 25° C. at one atmosphere and/or a material that has a boiling point at one atmosphere of at least about 300° C. "Volatile" means that the material exhibits a vapor pressure of at least about 0.2 mm of mercury at 20° C.

"Personal care product" or "personal care composition" means a product or composition suitable for topical application on mammalian keratinous tissue.

"Regulating skin condition" means improving skin appearance and/or feel, for example, by providing a benefit, such as a smoother appearance and/or feel. Herein, "improving skin condition" means effecting a visually and/or tactilely perceptible positive change in skin appearance and feel. The benefit may be a chronic or acute benefit and may include one or more of the following: reducing the appearance of wrinkles and coarse deep lines, fine lines, crevices, bumps, and large pores; thickening of keratinous tissue (e.g., building the epidermis and/or dermis and/or sub-dermal layers of the skin, and where applicable the keratinous layers of the nail and hair shaft, to reduce skin, hair, or nail atrophy); increasing the convolution of the dermal-epidermal border (also known as the rete ridges); preventing loss of skin or hair elasticity, for example, due to loss, damage and/or inactivation of functional skin elastin, resulting in such conditions as elastosis, sagging, loss of skin or hair recoil from deformation; reduction in cellulite; change in coloration to the skin, hair, or nails, for example, under-eye circles, blotchiness (e.g., uneven red coloration due to, for example, rosacea), sallowness, discoloration caused by hyperpigmentation, etc.

"Safe and effective amount" means an amount of a compound or composition sufficient to significantly induce a positive benefit, preferably a positive skin or feel benefit, including independently or in combinations the benefits disclosed herein, but low enough to avoid serious side effects (i.e., to provide a reasonable benefit to risk ratio, within the scope of sound judgment of the skilled artisan).

"Signs of skin aging," include, but are not limited to, all outward visibly and tactilely perceptible manifestations, as well as any macro- or micro-effects, due to keratinous tissue aging. These signs may result from processes which include, but are not limited to, the development of textural discontinuities such as wrinkles and coarse deep wrinkles, fine lines, skin lines, crevices, bumps, large pores, unevenness or roughness; loss of skin elasticity; discoloration (including undereye circles); blotchiness; sallowness; hyperpigmented skin regions such as age spots and freckles; keratoses; abnormal differentiation; hyperkeratinization; elastosis; collagen breakdown, and other histological changes in the stratum corneum, dermis, epidermis, vascular system (e.g., telangiectasia or spider vessels), and underlying tissues (e.g., fat and/or muscle), especially those proximate to the skin.

"Skin" means the outermost protective covering of mammals that is composed of cells such as keratinocytes, fibroblasts and melanocytes. Skin includes an outer epidermal layer and an underlying dermal layer. Skin may also include hair and nails as well as other types of cells commonly associated with skin, such as, for example, myocytes, Merkel cells, Langerhans cells, macrophages, stem cells, sebocytes, nerve cells and adipocytes.

"Skin-care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin-care active" means a compound or combination of compounds that, when applied to skin, provide an acute and/or chronic benefit to skin or a type of cell commonly found therein. Skin-care actives may regulate and/or improve skin or its associated cells (e.g., improve skin elasticity; improve skin hydration; improve skin condition; and improve cell metabolism).

"Skin-care composition" means a composition that includes a skin-care active and regulates and/or improves skin condition.

"Skin-care product" as used herein refers to a product that includes a skin-care composition. Some nonlimiting examples of "skin-care products" include skin creams, moisturizers, lotions, and body washes.

"Substantially free of" as used herein, means that the composition comprises less than 3% (e.g., less than 1%, less than 0.5%, less than 0.25%, or even less than 0.1%) by weight of the composition, of the stated ingredient.

"Substituted" means comprising at least one heteroatomic substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups.

"Topical application" means to apply or spread the compositions of the present invention onto the surface of the keratinous tissue.

Composition

Conventional skin care products that include relatively high levels of humectants such as glycerin commonly have undesirable feel and look characteristics when applied to skin, such as greasy or sticky feel and/or shiny appearance. The addition of particulate materials to these conventional products may address some of the look and feel problems, but typically have drawbacks of their own. Surprisingly, it has been discovered that a powder system that includes starch particles and is formulated to be applied as an overlying layer to a skin care product, as described in more detail below, can deliver desirable levels of feel and look benefits without the tradeoffs associated with some conventional powder systems.

The personal care composition disclosed herein is a stand-alone product that may be referred to as a "finisher" or "finisher composition." Finishers are generally recognized in the cosmetics industry as compositions that are applied as a topcoat or overlying layer to a basecoat or underlying layer of composition such as a skin care product. The present finisher may be used in conjunction with, for example, a moisturizer, conditioner, anti-aging product, skin-lightening product or other skin care product to improve the look and feel characteristics of such products. The finisher composition herein is applied as an overlying layer to an underlying layer of skin care composition. In some instances, the present finisher may be used in conjunction with an "all-in-one" type skin care product (i.e., a product that includes a skin care active such as glycerin and a powder system), or with a skin care product that does not include a powder system. As can be seen in the comparative examples below, simply incorporating a powder system into a skin care product may not sufficiently address the undesirable look and feel characteristics associated with one or more components in the product.

To provide a desired look benefit, the finisher compositions herein are formulated to have a chroma value of less than 10 (e.g., less than 6 or even less than 3), according to the Chroma method described in more detail below, and a Contrast Ratio (i.e., opacity) of less than 20 (e.g, less than 10 or even less than 6), according to the Contrast Ratio method described in more detail below. The chroma and contrast ratio of the composition is controlled at least in part by controlling the type, amount and particle size of the powders in the finisher composition. For example, in addition to providing a suitable type and amount of starch powder, it is also important to limit the amount and type of pigment particles and/or non-spherical particles in the finisher composition to provide the desired chroma and contrast ratio.

The present finisher is an oil-in-water ("O/W") emulsion comprising a continuous aqueous phase and a dispersed oil phase. The finisher also includes a suitable starch powder, which can be present in either phase. It may be desirable to disperse the starch particles in the oil phase, at least initially, since it is not uncommon for such particles to be generally hydrophobic. The aqueous phase of the present finisher composition includes water at an amount of from 20% to 85% (e.g., 30% to 80% or even from 40% to 75%) by weight of the finisher composition. The aqueous phase may include components other than water, such as water-soluble moisturizing agents, conditioning agents, anti-microbials, humectants and other water-soluble skin care actives, to impart an increased benefit to skin.

Non-volatile Oil

The oil phase of the finisher includes a non-volatile oil (e.g., non-volatile silicone oils, hydrocarbon oils, amides, esters, ethers and mixtures of these). In order to improve the skin appearance benefits provided by the finisher and minimize any undesirable visible tradeoffs (e.g., whitening), the starch particles must be at least partially wetted by the non-volatile oil. If the starch particles are applied to the target skin surface with no or too little non-volatile oil, the finisher may appear white, and thus any wrinkle or pore masking benefit provided by the finisher composition may be overshadowed by undesirable whiteness. On the other hand, if too much non-volatile oil is present, the skin may appear undesirably shiny, thus reducing or eliminating the skin textural masking benefit of the finisher (i.e., the ability of the finisher to help reduce the appearance of perceived skin flaws related to skin texture, such as wrinkles and pores). Accordingly, it is important to provide a suitable ratio of non-volatile oil to starch powder of between 1:10 and 3:2 (e.g., from 1:4 to 1:1 or even from 1:4 to 3:4).

The non-volatile oil herein should remain on this skin for a relatively long period of time (e.g., more than 2 hours, 4 hours or even more than 8 hours) without significant evaporation or absorption into the skin. if the oil evaporates, as a volatile oil would, or is absorbed into the skin, unwetted particles may be left on the skin resulting in undesirable whiteness. In addition, it may be desirable to select a non-volatile oil with a low refractive index, since high refractive index oils tend to make the skin appear shiny, which may reduce or even eliminate the skin textural masking benefit of the finisher.

In some instances, the oil phase of the finisher composition includes from more than 70% of a non-volatile silicone (e.g., more than 80%, more than 90% or even more than 95%). Non-volatile silicones suitable for use in the oil phase of the emulsion include, for example, polysiloxanes having a viscosity of from about 10 to about 1,000,000 centistokes at 25° C. Such polysiloxanes can be represented by the general chemical formula:

$$R_3SiO[R_2SiO]_xSiR_3$$

wherein R is independently selected from hydrogen or $C_{1-30}$ straight or branched chain, saturated or unsaturated alkyl, phenyl or aryl, trialkylsiloxy; and x is an integer from 0 to about 10,000. In some instances, R is methyl or ethyl. Particularly suitable polysiloxanes include polydimethylsiloxanes, which are also known as dimethicones, with viscosities of between 10 cst and 1000 cst, (e.g., between 15 cst to 400 cst or even between 20 cst and 200 cst). The average chain length for these preferred dimethicone materials is from 12 to 375 dimethylsiloxane units (e.g., from 20 to 200 or even from 27 to 125). Some non-limiting examples of such dimethicone materials include the DM-Fluid series available from Shin-Etsu, the Vicasil® series sold by Momentive Performance Materials Inc., and the Dow Corning® 200 series sold by Dow Corning Corporation (also sold as Xiameter® PMX-200 Silicone Fluids). Other suitable polysiloxanes include those represented by the chemical formula:

$$R_3SiO[R_2SiO]_x[RR'SiO]_ySiR_3$$

wherein R and R' are each independently hydrogen or $C_{1-30}$ straight or branched chain, saturated or unsaturated alkyl, aryl, or trialkylsiloxy; and x and y are each integers of 1 to 1,000,000. Examples include alkyl dimethicones wherein at least R' is a fatty alkyl (e.g., $C_{12-22}$). A suitable alkyl dimethicone is cetyl dimethicone, wherein R' is a straight C16 chain and R is methyl, commercially available as 2502 Cosmetic Fluid from Dow Corning.

Non-volatile hydrocarbon oils suitable for use herein may include straight, branched, or cyclic alkanes and alkenes. The chain length of such oils may be selected based on desired functional characteristics such as viscosity. Suitable non-volatile esters include esters with hydrocarbyl chains derived from fatty acids or alcohols (e.g., mono-esters, polyhydric alcohol esters, and di- and tri-carboxylic acid esters). The hydrocarbyl radicals of the esters hereof may include or have covalently bonded thereto other compatible functionalities, such as amides and alkoxy moieties (e.g., ethoxy or ether linkages, etc.). Exemplary esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, butyloctyl salicylate, phenylethyl benzoate, dicaprylyl carbonate, dioctyl malate, dicaprylyl maleate, isononyl isononanoate, propylene glycol dicaprate, diisopropyl adipate, dibutyl adipate, and oleyl adipate. Other suitable esters are further described in the Personal Care Product Council's *International Cosmetic Ingredient Dictionary and Handbook*, Thirteenth Edition, 2010, under the functional category of "Esters." Suitable non-volatile amides include compounds having an amide functional group while being liquid at 25° C. and insoluble in water. Suitable amides include, but are not limited to, N-acetyl-N-butylaminopropionate, isopropyl N-lauroylsarcosinate, butylphthalimide, isopropylphthalimide, and N,N,-diethyltoluamide. Other suitable amides are disclosed in U.S. Pat. No. 6,872,401. Suitable non-volatile ethers include saturated and unsaturated fatty ethers of a polyhydric alcohol, and alkoxylated derivatives thereof. Exemplary ethers include, but are not limited to, $C_{4-20}$ alkyl ethers of polypropylene glycols, and di-$C_{8-30}$ alkyl ethers. Suitable examples of these materials include PPG-14 butyl ether, PPG-15 stearyl ether, PPG-11 stearyl ether, dioctyl ether, dodecyl octyl ether, and mixtures thereof.

Spherical Starch Particles

The present finisher includes from 10% to 30% by weight of spherical starch particles (e.g., from 15% to 25% or even 20%) dispersed or suspended in a suitable carrier. The starch particles suitable for use herein may be coated or uncoated (e.g., coated with a suitable silicone material). Some non-limiting examples of commercially available starch particles suitable for use herein are tapioca starch (available as Tapioca Pure from AkzoNobel), corn starch (available as Purity 21C from AkzoNobel), potato starch, glyceryl starch (available as Dry-Ho GS from AkzoNobel), aluminum starch octenylsuccinate (available as Mackaderm ASTO-Dry from Rhodia, Inc., and Dry-Flo PC from AkzoNobel), calcium starch octenylsuccinate (available as Skin Flow C from MGP Ingredients, Inc., and Mackaderm CSTO-Dry from Rhodia, Inc.), and polymethylsilsesquioxane coated tapioca starch (available as Dry-Flo TS from AkzoNobel).

The starch particles give the finisher composition a silky or lubricious feel, which may offset the undesirable greasiness associated with oils and/or the undesirable tacky feel associated with some humectants. In addition, the present powder system provides a light scattering effect that provides a smooth look to the skin that is often more natural looking than makeup. Regarding the powder concentration ranges disclosed herein, if too much starch powder is present then the look and feel benefits provided by the finisher can level off or even start to decline. In particular, the powder may no longer remain evenly distributed on the skin surface, which can lead to undesirable whitening (e.g., because powders no longer remain wetted) and/or flaking from the skin (e.g., because the powders no longer suitably adhere to the rest of the product film). On the other hand, if too little starch powder is present then the undesirable look and/or feel properties of the underlying skin care composition may not be altered as desired.

It is believed, without being limited by theory, that the size of the starch particles is also important for delivering visible texture benefits on skin. In particular, is important that the particles are large enough to protrude from the film formed by the skin care product when applied to the skin (i.e., at least a portion of each (or most) starch particle(s) extends out of the surface of the film). In this way, a "rough" film is created, which diffusely reflects light and reduces the surface area of the underlying skin care product film that can be contacted by a user's hand or other object (i.e., reduces the tacky and/or greasy feel of the skin care composition, etc.). But as particle size increases, the number of particles in the finisher composition decreases. For substantially spherical particles, the number of particles per unit volume is proportional to the inverse of the cube of the particle diameter. Thus, using relatively large particles at a fixed amount (i.e., weight percent) of powder in the product effectively reduces the number of particles that can be added. On the other hand, using smaller particles may increase the number of particles present in the finisher, but may not provide the desired "rough surface" to the product film because a smaller portion of each particle (or even no portion of the particle) extends above the surface of the product film. Consequently, it is important to ensure that the selected particle size is appropriate for the skin care product it is intended to be used with.

On average, it is believed, without being limited by theory, that the film thickness of conventional skin care products, when used as intended, is generally between 1 and 6 microns. Accordingly, the starch particles herein may have a median particle size of from 5 µm to 30 µm, (e.g., from 8 µm to 25 µm or even from 10 µm to 20 µm). Of course, it is to be appreciated that the particle sizes disclosed herein may be readily adapted for use with thicker or thinner films without departing from the spirit and scope of the present invention. Particle size can be determined by any suitable method known in the art, such as by using coulter-counter equipment or the ASTM Designation E20-85, titled "Standard Practice for Particle Size Analysis of Particulate Substances in the Range of 0.2 to 75 Micrometers by Optical Microscopy," ASTM Volume 14.02, 1993. The particle sizes disclosed herein are volume-weighted mean particle sizes.

The starch particles herein are substantially spherical (i.e., the majority or even all the particles in the finisher composition are spherical). It is believed, without being limited by theory, that spherical particles generally provide a more suitable product feel relative to non-spherical particles, at least in part because a spherical particle creates less drag and roll more smoothly across a surface than the non-spherical particle. As used herein, "spherical" and "sphere" mean particles that have an aspect ratio (i.e., ratio of major axis to minor axis) of from 1:1 to 2:1, (e.g., 1:1 to 2:1, 1:1 to 1.6:1 or even 1:1 to 1.4:1). The shape of the particles may be determined by any suitable method known in the art (e.g., optical microscope or electron microscope and suitable image analysis software).

Other Spherical Particles

In some instances, the finisher may, optionally, include other spherical particles in addition to the spherical starch particles herein. For example, the finisher may include spherical silicone elastomer particles such as those disclosed in U.S. Provisional App. 61/927,231.

In some instances, the finisher may, optionally, include non-spherical particles (e.g., non-spherical silicone elastomer particles, mica, talc, clay). However, the finisher generally includes less than 4% of non-spherical particles (e.g., less than 3% or even less than 1%). When referring to non-spherical silicone elastomer particles, the indicated percentages are understood to refer to amount of dry elastomer, as opposed to the total amount of elastomer and solvent, used for example for storage and shipping. Exemplary non-spherical crosslinked siloxane elastomers include the CTFA (Cosmetic, Toiletry, and Fragrance Association *International Cosmetic Ingredient Dictionary and Handbook*, 11$^{th}$ ed.) designated dimethicone/vinyl dimethicone crosspolymers supplied by a variety of suppliers including Dow Corning™, General Electric™, Shin Etsu™ (KSG 15 and 16), and Grant Industries. Other exemplary non-emulsifying crosslinked siloxane elastomer include the CTFA designated dimethicone crosspolymers including Dow Corning™; e.g. DC 9040 and DC 9045 which are supplied as a 12.5% elastomers in cyclomethicone, and DC 9041 which is supplied as 16% elastomer in dimethicone).

The amount of pigment present in the finisher composition should be kept relatively low in order to avoid the undesirable aesthetics associated with higher levels of pigment (e.g., whiteness, flaking and lower spreadability). Finisher compositions herein may generally include less than 1%, (e.g., less than 0.5% or even less than 0.1%) by weight of particles that impart chroma and/or opacity to the composition (e.g., pigment grade titanium dioxide or iron oxide). In some instances, the present finisher is free of pigment and/or other colorants (e.g., lakes and dyes). Exemplary pigments can be found in the Personal Care Product Council's *International Cosmetic Ingredient Dictionary and Handbook*, Thirteenth Edition, 2010.

The present finisher may also include one or more optional ingredients that are commonly used in personal care compositions, such as volatile oils, emulsifiers, thickeners, skin care actives, combinations of these and the like. In particular, it may be desirable in some instances to include a volatile oil at up to 30 wt % (e.g., from 5% to 20%). The volatile oil may be a volatile silicone, a volatile hydrocarbon oil or a combination of these.

Volatile silicones include cyclic and linear volatile silicones. A description of various volatile silicones is found in Todd, et al. "Volatile Silicone Fluids for Cosmetics", 91 Cosmetics and Toiletries 27-32 (1976). Suitable cyclic volatile silicones include cyclic dimethyl siloxane chains containing an average of from about 3 to about 5 silicon atoms, preferably from about 4 to about 5 silicon atoms. Exemplary cyclic volatile silicones of varying viscosities include Dow Corning DC 244, DC 245, DC 344, and DC 345; GE Silicones-OSi Specialties Volatile Silicone 7207 and Volatile Silicone 7158; and GE Silicones SF1202. Suitable volatile linear silicones include the polydimethylsiloxanes containing an average of from about 2 to about 8 silicon atoms. Exemplary linear volatile silicones include the Dow Corning DC 200 series with viscosities of 0.65 cst, 1.0 cst, and 2.0 cst. In certain embodiments, the linear volatile silicones generally have viscosities of less than or equal to about 4 centistokes at 25° C., and the cyclic materials generally have viscosities of less than about 6 centistokes at 25° C.

Some non-limiting examples of suitable volatile hydrocarbon oils include isododecane (e.g., Permethyl-99A which is available from Presperse Inc.), isodecane, and the C7-C8 through C12-C15 isoparaffins (e.g., Isopar Series available from Exxon Chemicals).

The finisher composition here may optionally include a humectant such as glycerin; however, the amount should be low enough to enable the finisher to provide the desired look and feel benefit to the underlying skin product. In some instances, the optional humectant may be present at an amount of less than 10% or even less than 5%. In some instances, the finisher is free of humectants. An exemplary class of humectants is polyhydric alcohols such as polyalkylene glycols, alkylene polyols and derivatives of these (e.g., propylene glycol, dipropylene glycol, polypropylene glycol, polyethylene glycol and derivatives thereof; glycerin, sorbitol; hydroxypropyl sorbitol; erythritol; threitol; pentaerythritol; xylitol; glucitol; mannitol; butylene glycol (e.g., 1,3-butylene glycol); pentylene glycol; hexane triol (e.g., 1,2,6-hexanetriol); ethoxylated glycerine; and propoxylated glycerine).

TEST METHODS

Chroma Method

This method provides a suitable means for measuring the color properties of a film formed from a personal care composition. Herein, "chroma," describes color and color intensity. For the purposes of the present disclosure, color is defined according to a value on the well known CIELAB color system.

To measure the color of personal care composition, a substantially uniform film of the composition is first created on a standard background. The film is created by applying the product to a standard opacity chart (e.g., Form N2A, Leneta Company of Manwah, N.J. or the equivalent thereof, of which the top half is black and the bottom half is white) and then spread on the black area of the opacity chart using a Bird film applicator with a thickness of 254 µm (e.g., as commercially available from BYK Gardner of Columbia, Md., or the equivalent thereof).

The color (L, a, and b values) of the product film is then measured using a spectrophotometer with settings selected to exclude specular reflection. Chroma is measured by a vector having its origin at the intersection of the red-green and blue-yellow axes and extending outward into the color space defined by the horizontal and vertical axes of the CIELAB color system. The length of the vector represents the chroma, and the direction of the vector represents the shade, or hue. The shorter the vector, the less colored is the composition, and the lower the chroma.

Contrast Ratio

This method provides a suitable means for determining the opacity of a composition. To measure the contrast ratio of a composition, the composition is applied to a standard opacity chart (e.g., Form N2A, Leneta Company of Manwah, N.J.) and then spread to form a substantially uniform film using a Bird film applicator with a thickness of 38.1 microns (e.g., as commercially available from BYK Gardner of Columbia, Md., or the equivalent thereof). The film is allowed to dry for 1 hour under conditions of 22° C.+/−1° C., 1 atm. Using a spectrophotometer, the Y tristimulus value (i.e., the XYZ color space of the film) of the product film is measured and recorded. The Y tristimulus value is measured in three different areas of the product film over the black section of the opacity chart, and also in three different areas of the product film over the white section of the opacity chart.

The contrast ratio is calculated as the mathematical average of the three Y tristimulus values over the black areas, divided by the mathematical average of the three Y tristimulus values over the white areas, times 100:

$$\text{Contrast Ratio} = \frac{\text{average }(Yblack)}{\text{average }(Ywhite)} \times 100$$

Visual Attribute Test (VAT)

The visible attribute test (VAT) is a technical panel used to quantify visible benefits of the finisher compositions herein when applied to facial skin. Fifteen to thirty female panelists who are pre-screened to have moderate or higher baseline levels of facial attributes such as fine lines, wrinkles, bumpy surface texture, and pores participate in each VAT study. Two trained expert graders then grade various attributes on each panelist's face both at baseline and 10 minutes after application of 0.45 grams of product to one side of the face. Reductions in facial attributes are then calculated as pre-treatment grade minus the post-treatment grade, and the significance of the differences are determined using ANOVA procedures (Tukey's HSD test).

A hypothetical data table representing typical VAT data calculations for bumpy surface texture is shown in Table 1 below. For fine lines, wrinkles, bumpy surface texture and/or pores, a difference of greater than approximately 0.4 provides consumer noticeable changes.

TABLE 1

| Panelist Number | Pre-Treatment Grade | Post-Treatment Grade | Delta (Pre Minus Post) |
|---|---|---|---|
| 1 | 3.65 | 3.15 | 0.5 |
| 2 | 3.5 | 2.95 | 0.55 |
| 3 | 4.1 | 3.2 | 0.9 |
| 4 | 4.5 | 3.85 | 0.65 |
| 5 | 3.7 | 2.8 | 0.9 |

The facial attributes evaluated by the expert graders include the following:

Lines/Wrinkles—Severity of the skin on the cheek areas caused by fine lines and wrinkles. The cheek area includes that which is below the top of the cheek bone, excluding skin around the mouth. Features of this attribute include the number, length, depth, and percent coverage of the lines and wrinkles. Does not encompass pores directly, but does include lines which appear to be formed by interconnected pores. Each of the features of this attribute are equally weighted.

Bumpy Surface—Skin unevenness or roughness associated with a "pebbled" or an "orange peel" surface. Based on both the degree of roughness as defined as height and proximity and the percentage of the face covered by the surfaced appearance. Roughness and coverage are equally weighted in the final grade. Does not include obviously raised brown moles.

Pores—Coverage and intensity of the facial pores. Coverage is defined as the percentage of the entire cheek areas that possess visible pores (open holes). Intensity is defined as the quantity of pores and the average pore size where larger pores drive higher scores. Both elements of this attribute are equally weighted in the final grade.

Brightness—The brightening feature increases the lightness and luminescence of the face. It may be accompanied by a reduction in red and brown tones.

The expert graders rate each of the above attributes both pre- and post-treatment using the 5 point continuous line scale shown below:

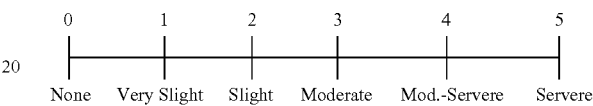

EXAMPLES

Examples 1-5

The following representative examples illustrate finisher compositions according to the present disclosure. The compositions in these examples are prepared by first combining the water phase ingredients in a container and mixing until uniform. The thickener is added and the water phase is mixed until uniform, and then the pH adjuster, if present, is added and the water phase is again mixed until uniform. The oil phase ingredients are combined in a separate container and mixed until uniform. The powders are next added to the oil phase and the combination is mixed until uniform. Finally, the oil/powder phase is added to the water phase and the resulting emulsion is subjected to high shear mixing (e.g., Flacktek Speedmixer, or rotor-stator mill) Table 2 shows the ingredients used to make Examples 1-5.

TABLE 2

|  | Example 1 | Example 2 | Example 3 | Example 4 | Example 5 |
|---|---|---|---|---|---|
| Water Phase: |  |  |  |  |  |
| Water | 49.86 | 50.36 | 64.16 | 60.56 | 56.85 |
| Disodium EDTA | 0.05 | 0.05 | 0.05 | 0.05 | 0.05 |
| Methylparaben | — | — | — | 0.1 | — |
| Symdiol 68[1] | 0.7 | 0.7 | 0.7 | — | — |
| Glycacil L[2] | 0.09 | 0.09 | 0.09 | 0.09 | — |
| Phenoxyethanol | — | — | 0.2 | 0.5 | — |
| Glydant Plus Liquid[3] | — | — | — | — | 0.3 |
| pH Adjustor: |  |  |  |  |  |
| Triethanolamine | — | — | — | 0.2 | — |
| Thickener: |  |  |  |  |  |
| Sepigel 305[4] | — | — | 0.5 | 1.0 | — |
| Simulgel INS-100[5] | 2.0 | 1.5 | 1.0 | — | — |
| Makimousse-12[6] | — | — | — | — | 0.4 |
| Ultrez 10[7] | — | — | — | 0.1 | — |
| Ultrez 21[8] | — | — | — | 0.1 | — |
| Xanthan gum | — | — | — | — | 0.1 |
| Oil Phase: |  |  |  |  |  |
| Cyclomethicone D5 | 6.0 | 12.0 | — | 5.0 | 10.0 |
| Dimethicone 2 cst | — | — | 5.0 | — | — |

TABLE 2-continued

| | Example 1 | Example 2 | Example 3 | Example 4 | Example 5 |
|---|---|---|---|---|---|
| Dimethicone 20 cst | — | — | 3.0 | — | — |
| Dimethicone 50 cst | 10.0 | 10.0 | — | 12.0 | 8.0 |
| Dimethicone 350 cst | — | — | 3.0 | — | — |
| DE-23[9] | — | — | 3.0 | — | — |
| DC 5562[10] | — | — | — | — | 2.0 |
| DC1503[11] | — | — | — | — | 2.0 |
| DC9045[12] | 11.0 | — | 4.0 | — | — |
| Laureth-4 | 0.3 | 0.3 | 0.3 | 0.3 | 0.3 |
| Particles: | | | | | |
| Dry Flo TS[13] | 20.0 | 25.0 | 15.0 | — | 10.0 |
| Tapioca Pure[14] | — | — | — | 20.0 | 5.0 |
| Dry Flo Pure[15] | — | — | — | — | 5.0 |
| Total: | 100% | 100% | 100% | 100% | 100% |

[1]1,2-hexanediol and caprylyl glycol, from Symrise
[2]Iodopropynyl butylcarbamate, PEG-4 laurate, PEG-4 dilaurate, and polyethylene glycol, from Lonza
[3]DMDM Hydantoin, Butane-1,3-diol, iodopropynyl butylcarbamate, water, from Lonza
[4]Polyacrylamide, C13-14 isoparaffin, and laureth-7, from Seppic
[5]Sodium acrylate/sodium acryloyldimethyl taurate copolymer, isohexadecane, and polysorbate 60, from Seppic
[6]Sodium polyacrylate starch, from Kobo Products Inc.
[7]Carbomer, from Lubrizol
[8]Acrylates C10-/30 alkyl acrylate crosspolymer, from Lubrizol
[9]Polydiethylsiloxane, from Gelest
[10]Bis-hydroxyethoxypropyl dimethicone, from Dow Corning
[11]Dimethicone and dimethiconol, from Dow Corning
[12]Cyclopentasiloxane and dimethicone crosspolymer, from Dow Corning
[13]Tapioca and polymethylsilsesquioxane, from Akzo Nobel
[14]Tapioca powder, from Akzo Nobel
[15]Aluminum starch octenyl succinate, from Akzo Nobel All data provided in the examples that follow are determined according to the VAT test described above and are statistically significant to an 80% confidence level (at alpha=0.20, Tukey tests).

Examples 6 and 7

Impact of Glycerin

Examples 6 and 7 demonstrate the undesirable effect of high levels of humectant on the appearance attributes of a skin care product. The compositions in Examples 6 and 7 contain the same high level of silicone elastomer particles and non-volatile silicone oil, and are otherwise identical except that Example 6 contains 5% glycerin while Example 7 contains 25% glycerin.

The compositions in Examples 6 and 7 are prepared by first combining the water phase ingredients and thickener in a container and mixing until uniform. The oil phase ingredients are combined in a separate container and mixed until uniform. The particulates are next added to the oil phase and the combination is mixed until uniform. Finally, the oil/particulate phase is added to the water phase and the resulting emulsion is subjected to high shear mixing (e.g., Flacktek Speedmixer, or rotor-stator mill) Table 3 shows the ingredients used in the compositions of Examples 6 and 7.

TABLE 3

| | Example 6 | Example 7 |
|---|---|---|
| Water Phase: | | |
| Water | 20.84 | 0.84 |
| Glycerin | 5.0 | 25.0 |
| Disodium EDTA | 0.05 | 0.05 |
| Glydant Plus Liquid[1] | 0.3 | 0.3 |
| Niacinamide | 2.0 | 2.0 |
| D-panthenol | 0.5 | 0.5 |
| Laureth-4 | 0.2 | 0.2 |
| Thickener: | | |
| Simulgel INS-100[2] | 2.0 | 2.0 |
| Oil Phase: | | |
| Cyclomethicone D5 | 24.2 | 22.42 |
| Dimethicone 50 cst | 4.39 | 4.39 |
| DC9045[3] | 11.0 | 11.0 |
| Isopropyl lauroyl sarcosinate | 7.32 | 7.32 |
| Polysorbate 60 | 0.2 | 0.2 |
| Particles: | | |
| KSP 102[4] | 11.0 | 11.0 |
| KSP 105[5] | 11.0 | 11.0 |
| Total: | 100% | 100% |

[1]DMDM Hydantoin, Butane-1,3-diol, iodopropynyl butylcarbamate, water, from Lonza
[2]Sodium acrylate/sodium acryloyldimethyl taurate copolymer, isohexadecane, and polysorbate 60, from Seppic
[3]Cyclopentasiloxane and dimethicone crosspolymer, from Dow Corning
[4]Vinyl dimethicone/methicone silsesquioxane crosspolymer, from Shin Etsu
[5]Vinyl dimethicone/methicone silsesquioxane crosspolymer, from Shin Etsu The compositions of Examples 6 and 7 were then placed in a Visual Attribute Test (VAT) to compare their effectiveness at reducing the appearance of various facial attributes. As can be seen from the results of this testing, summarized in Table 4 below, increasing the level of glycerin from 5% to 25% significantly reduced the appearance attributes of these products in use.

Larger VAT scores for cheek fine lines, bumpy surface, and pores correspond to bigger visible reductions in the appearance of these attributes. Thus, these data clearly demonstrate the negative impact that high levels of glycerin can have on the appearance benefits of a skin care product.

TABLE 4

|  | Example 6 5% Glycerin | Example 7 25% Glycerin |
| --- | --- | --- |
| Cheek Fine Lines | 0.40 | 0.18 |
| Bumpy Surface | 0.29 | 0.09 |
| Pores | 0.27 | 0.09 |

Examples 8-12

Impact of Layers

Examples 8, 9, 10, 11, and 12 demonstrate the effects of combining a moisturizing composition (i.e., conventional skin care product) with a particulate composition in an "all-in-one" composition versus applying the present finisher composition as a standalone product to an underlying layer of a skin care composition in a two-step process. The compositions used in Examples 8 and 9 are prepared by first combining the water phase ingredients and thickener in a container and mixing until uniform. The oil phase ingredients are combined in a separate container and mixed until uniform. The particulates are next added to the oil phase and the combination is mixed until uniform. Finally, the oil/particulate phase is added to the water phase and the resulting emulsion is subjected to high shear mixing (e.g., Flacktek Speedmixer, or rotor-stator mill). The skin care compositions of Examples 10 and 11 are prepared by combining all of the water phase ingredients and pH adjuster, mixing until uniform and warming if necessary. Next, the thickeners are added and the compositions are again mixed until uniform. Example 12 is prepared in substantially the same way as Example 1-5 above. The ingredients of each composition are shown below in Table 5.

TABLE 5

|  | Example 8 All-in-One | Example 9 All-in-One w/Actives | Example 10 First Layer - No powder | Example 11 First Layer w/Actives - No powder | Example 12 Inventive Finisher |
| --- | --- | --- | --- | --- | --- |
| Water Phase: | | | | | |
| Water | 38.36 | 28.78 | 76.685 | 68.88 | 49.36 |
| Glycerin | 15.0 | 15.0 | 15.0 | 15.0 | — |
| Disodium EDTA | 0.05 | 0.05 | 0.025 | 0.05 | 0.05 |
| Symdiol 68[1] | 0.7 | 1.0 | 0.7 | 1.0 | 0.7 |
| Glycacil L[2] | 0.09 | 0.09 | 0.09 | 0.09 | 0.09 |
| Niacinamide | 5.0 | 5.0 | 5.0 | 5.0 | — |
| D-panthenol | 0.5 | 1.0 | 0.5 | 1.0 | — |
| Sepiwhite MSH[3] | — | 0.2 | — | 0.2 | — |
| Glyco-Repair[4] | — | 3.0 | — | 3.0 | — |
| Biomyox[5] | — | 2.0 | — | 2.0 | — |
| Palestrina[6] | — | 1.15 | — | 1.15 | — |
| Inositol | — | 1.5 | — | 1.5 | — |
| pH Adjuster: | | | | | |
| Triethanolamine | — | 0.13 | — | 0.13 | — |
| Thickener: | | | | | |
| Simulgel INS-100[7] | 1.6 | 2.4 | 2.0 | — | 1.5 |
| Makimousse-12[8] | — | — | — | 1.0 | — |
| Oil Phase: | | | | | |
| Cyclomethicone D5 | 8.0 | 8.0 | — | — | 12.0 |
| Dimethicone 50 cst | 5.0 | 5.0 | — | — | 5.0 |
| DC1503[9] | — | — | — | — | — |
| DC9045[10] | 5.5 | 5.5 | — | — | 11.0 |
| Laureth-4 | 0.2 | 0.2 | — | — | 0.3 |
| Particles: | | | | | |
| Dry Flo TS[11] | 20.0 | 20.0 | — | — | 20.0 |
| Total: | 100% | 100% | 100% | 100% | 100% |

[1] 1,2-hexanediol and caprylyl glycol, from Symrise
[2] Iodopropynyl butylcarbamate, PEG-4 laurate, PEG-4 dilaurate, and polyethylene glycol, from Lonza
[3] Undecylenoyl phenylalanine, from Seppic
[4] Water and hydrolyzed *ceratonia siliqua* seed extract, from Silab
[5] Water and *nasturtium officinale* extract, from Silab
[6] Water, glycerin, decyl glucoside, lactic acid, benzyl alcohol, and palmitoyl dipeptide-7, from Sederma (France)
[7] Sodium acrylate/sodium acryloyldimethyl taurate copolymer, isohexadecane, and polysorbate 60, from Seppic
[8] Sodium polyacrylate starch, from Kobo Products Inc.
[9] Dimethicone and dimethiconol, from Dow Corning
[10] Cyclopentasiloxane and dimethicone crosspolymer, from Dow Corning
[11] Tapioca and polymethylsilsesquioxane, from Akzo Nobel The skin care composition in Example 8 is an all-in-one formulation that contains the same glycerin and skin active levels as the skin care composition of Example 10. The skin care composition of Example 9 is an all-in-one formulation that contains the same glycerin and skin active levels as the skin care composition of Example 11. Example 12 is an example of the present finisher composition. Examples 8 and 9 also include the starch powder system of Example 12. A key difference between the compositions of Examples 8 and 10 compared to the compositions of Examples 9 and 11 is that the latter compositions contain additional skin active ingredients (Sepiwhite MSH, Glyco-Repair, Biomyox, Palestrina, and Inositol). The relationships between the compositions of Examples 8 through 12 are summarized in Table 6 below. Note also that for the all-in-one versus two step comparisons, a few very minor formula adjustments were made to ensure adequate stability and physical properties. However, these minor formula adjustments are not expected to significantly impact the appearance attributes of these formulations.

TABLE 6

|  | All-in-One Composition | Two Step |
| --- | --- | --- |
| Low Skin Actives | Example 8 | Step 1: Example 10 |
|  |  | Step 2: Example 12 |
| High Skin Actives | Example 9 | Step 1: Example 11 |
|  |  | Step 2: Example 12 |

The all-in-one compositions above (Examples 8 and 9) and their corresponding two step compositions (Examples 10+12 and 11+12) were then placed in a Visual Attribute Test (VAT) to compare their effectiveness at reducing the appearance of various facial attributes. For simplicity and to increase statistical power, the results of both of these all-in-one to two step comparisons have been combined in Table 7 below. As can be seen from the results, the two-step approach provides significantly greater visible benefits than the corresponding all-in-one system, despite both all-in-one and two step systems containing the same starch powder and non-volatile silicones (note that negative values for brightness correspond to an increase in brightness of the facial skin). Thus, these results demonstrate the benefits of applying the present finisher over an underlying layer of a skin care product.

TABLE 7

|  | All-in-One Compositions Examples 8 and 9 | Two-Step Examples 10 + 12 Examples 11 + 12 |
| --- | --- | --- |
| Bumpy Surface | 0.43 | 0.61 |
| Pores | 0.55 | 0.68 |
| Brightness | −0.34 | −0.62 |

Examples 13 and 14

Impact of Non-volatile Oil to Powder Ratio

The following are examples of the powder layer compositions according to the present invention, both of which contain 20% starch particles, similar to Example 12 above. A key difference between Example 12 above and Examples 13 and 14, is the non-volatile oil (50 cst dimethicone) to powder ratio. Note that a few very minor adjustments were made to these formulations to ensure that they had similar physical properties and stability, but these adjustments are not expected to impact product performance. Examples 13 and 14 are prepared in substantially the same manner as described above. Table 8 shows the ingredients used in Examples 13 and 14.

TABLE 8

|  | Example 13 | Example 14 |
| --- | --- | --- |
| Water Phase: |  |  |
| Water | 44.36 | 40.56 |
| Disodium EDTA | 0.05 | 0.05 |
| Symdiol 68[1] | 0.7 | 0.7 |
| Glycacil L[2] | 0.09 | 0.09 |
| Thickener: |  |  |
| Simulgel INS-100[3] | 1.5 | 1.3 |
| Oil Phase: |  |  |
| Cyclomethicone D5 | 12.0 | 6.0 |
| Dimethicone 50 cst | 10.0 | 20.0 |
| DC9045[4] | 11.0 | 11.0 |
| Laureth-4 | 0.3 | 0.3 |
| Particles: |  |  |
| Dry Flo TS[5] | 20.0 | 20.0 |
| Total: | 100% | 100% |

[1]1,2-hexanediol and caprylyl glycol, from Symrise
[2]Iodopropynyl butylcarbamate, PEG-4 laurate, PEG-4 dilaurate, and polyethylene glycol, from Lonza
[3]Sodium acrylate/sodium acryloyldimethyl taurate copolymer, isohexadecane, and polysorbate 60, from Seppic
[4]Cyclopentasiloxane and dimethicone crosspolymer, from Dow Corning
[5]Tapioca and polymethylsilsesquioxane, from Akzo Nobel The compositions in Examples 12, 13, and 14 were placed in a VAT study as part of a two-step process, using the composition of Example 10 as the underlying skin care product for each test. As can be seen from the results of this testing, summarized in Table 9 below, as the non-volatile oil-to-powder ratio increased, the appearance attributes provided by these compositions worsened. Thus, this data clearly shows the benefit of the preferred nonvolatile oil to powder ratio in the finisher compositions herein.

TABLE 9

|  | Example 10 + Example 12 | Example 10 + Example 13 | Example 10 + Example 14 |
| --- | --- | --- | --- |
| Non-Volatile Oil to Powder Ratio | 1:4 | 1:2 | 1:1 |
| Cheek Fine Lines | 0.67 | 0.54 | 0.36 |
| Bumpy Surface | 0.67 | 0.58 | 0.33 |
| Brightness | −0.70 | −0.50 | −0.27 |

Example 15

Impact of Order of Layers

This example demonstrates the importance of applying the present finisher as an overlying layer to an underlying layer of a skin care product, and not the other way around. The composition used in Example 15 is made by first combining the water phase ingredients and mixing until uniform. Next, the thickener is added and the composition is again mixed until uniform. Table 10 shows the ingredients used to make the composition in Example 15.

TABLE 10

|  | Example 15 |
| --- | --- |
| Water Phase: |  |
| Water | 78.16 |
| Glycerin | 15.0 |
| Disodium EDTA | 0.05 |
| Symdiol 68[1] | 0.7 |
| Glycacil L[2] | 0.09 |
| Niacinamide | 5.0 |
| D-panthenol | 0.5 |
| Thickener: |  |
| Makimousse-12[3] | 0.5 |
| Total: | 100% |

[1]1,2-hexanediol and caprylyl glycol, from Symrise
[2]Iodopropynyl butylcarbamate, PEG-4 laurate, PEG-4 dilaurate, and polyethylene glycol, from Lonza
[3]Sodium polyacrylate starch, from Kobo Products Inc.

Using the composition in Example 15, along with the compositions in previous Examples 10 and 12, a VAT study was conducted to understand the impact of the order in which the layers of the two step systems are applied to skin. Table 11 shows the two step systems placed in the VAT study:

TABLE 11

|  | Step 1 Composition (underlying layer) | Step 2 Composition (overlying layer) |
| --- | --- | --- |
| Intended Application | 10 | 12 |
| Reversed Application | 12 | 15 |

Note that Examples 10 and 15 differ from one another only in the thickener used, and this difference is not expected to have a significant impact on the optical benefit demonstrated in this test. As can be seen from the VAT results in Table 12 below, applying the finisher as an overlying layer delivered suitable benefits for the various visible attributes tested. However, applying the finisher as the underlying layer provided significantly less visible benefit. Thus, these results confirm the importance of the order of application steps of the current invention.

TABLE 12

|  | Reversed Application | Intended Application |
| --- | --- | --- |
| Cheek Fine Lines | 0.35 | 0.67 |
| Bumpy Surface | 0.28 | 0.67 |
| Brightness | −0.23 | −0.70 |

Examples 16-19

Amount of Starch

This example demonstrates the importance of including the appropriate amount of starch powder in the finisher. The compositions used in Example 16-19 are prepared in substantially the same way as described previously for these types of compositions. Table 13 shows the ingredients used to make the compositions in Examples 16-19.

TABLE 13

|  | Example 16 First Layer No Powder | Example 17 Inventive Finisher - 10% | Example 18 Inventive Finisher - 20% | Example 19 Inventive Finisher - 30% |
| --- | --- | --- | --- | --- |
| Water Phase: |  |  |  |  |
| Water | 76.685 | 65.46 | 49.36 | 40.86 |
| Glycerin | 15.0 |  |  |  |
| Disodium EDTA | 0.025 | 0.05 | 0.05 | 0.05 |
| Symdiol 68[1] | 0.7 | 0.7 | 0.7 | 0.7 |
| Glycacil L[2] | 0.09 | 0.09 | 0.09 | 0.09 |
| Niacinamide | 5.0 | — | — | — |
| D-panthenol | 0.5 | — | — | — |
| Thickener: |  |  |  |  |
| Simulgel INS-100[3] | 2.0 | 2.0 | 1.5 | 1.5 |
| Oil Phase: |  |  |  |  |
| Cyclomethicone D5 | — | 8.0 | 12.0 | 8.0 |
| Dimethicone 50 cst | — | 2.5 | 5.0 | 7.5 |
| DC9045[4] | — | 11.0 | 11.0 | 11.0 |
| Laureth-4 | — | 0.2 | 0.3 | 0.3 |
| Particles: |  |  |  |  |
| Dry Flo TS[5] | — | 10.0 | 20.0 | 30.0 |
| Total: | 100% | 100% | 100% | 100% |

[1]1,2-hexanediol and caprylyl glycol, from Symrise
[2]Iodopropynyl butylcarbamate, PEG-4 laurate, PEG-4 dilaurate, and polyethylene glycol, from Lonza
[3]Sodium acrylate/sodium acryloyldimethyl taurate copolymer, isohexadecane, and polysorbate 60, from Seppic
[4]Cyclopentasiloxane and dimethicone crosspolymer, from Dow Corning
[5]Tapioca and polymethylsilsesquioxane, from Akzo Nobel Table 14 shows the test results from this testing. As seen in Table 14, the benefit indicates an improvement trend from 10% starch to 20% starch, but the benefit decreases from 20% to 30% starch.

TABLE 14

|  | Average VAT Score | | |
| --- | --- | --- | --- |
|  | 10% Starch | 20% Starch | 30% Starch |
| Cheek Fine Lines | 0.44 | 0.67 | 0.58 |
| Bumpy Surface | 0.43 | 0.67 | 0.52 |
| Pores | 0.46 | 0.68 | 0.61 |

Examples 20 and 21

Impact of Increased Opacity

The following two examples demonstrate the undesirable appearance effects caused by a high opacity. The examples utilize a spherical silicone elastomer powder system, but it is believed that the starch powder system of the present invention would generally provide the same results. Examples 20 and 21 both contain the same high level of silicone elastomer spherical particles and non-volatile silicone oil, and are identical except that example 21 contains 3.43% pigments while example 20 does not contain pigments. The pigments used in example 21 resulted in increased opacity compared to example 20. Opacity is assessed by measuring contrast ratio (the higher the contrast ratio, the higher the level of opacity). Example 21 has a contrast ratio of 34, while example 20 has a contrast ratio of 4.3. Examples 20 and 21 are prepared using the ingredients shown in Table 15 in substantially the same way as described above for these types of compositions.

TABLE 15

|  | Example 20 | Example 21 |
|---|---|---|
| Water Phase: | | |
| Water | 21.04 | 21.04 |
| Glycerin | 5.0 | 5.0 |
| Disodium EDTA | 0.05 | 0.05 |
| Glydant Plus Liquid[1] | 0.3 | 0.3 |
| Niacinamide | 2.0 | 2.0 |
| D-panthenol | 0.5 | 0.5 |
| Thickener: | | |
| Simulgel INS-100[2] | 2.0 | 2.0 |
| Oil Phase: | | |
| Cyclomethicone D5 | 24.2 | 20.77 |
| Dimethicone 50 cst | 4.39 | 4.39 |
| DC9045[3] | 11.0 | 11.0 |
| Isononyl Isononanoate | 7.32 | 7.32 |
| Laureth-4 | 0.2 | 0.2 |
| Powders: | | |
| KSP 102[4] | 11.0 | 11.0 |
| KSP 105[5] | 11.0 | 11.0 |
| Pigments: | | |
| Titanium Dioxide[6] | — | 3.0 |
| Iron Oxides CI 77491[7] | — | 0.1 |
| Iron Oxides CI 77492[8] | — | 0.33 |
| Total: | 100% | 100% |

[1]DMDM Hydantoin, Butane-1,3-diol, iodopropynyl butylcarbamate, water, from Lonza
[2]Sodium acrylate/sodium acryloyldimethyl taurate copolymer, isohexadecane, and polysorbate 60, from Seppic
[3]Cyclopentasiloxane and dimethicone crosspolymer, from Dow Corning
[4]Vinyl dimethicone/methicone silsesquioxane crosspolymer, from Shin Etsu
[5]Vinyl dimethicone/methicone silsesquioxane crosspolymer, from Shin Etsu
[6]Titanium Dioxide, Isohexadecane, Polyhydroxystearic Acid, Triethoxycaprylylsilane
[7]Iron Oxides CI 77491, Cyclopentasiloxane, Methicone, PEG/PGG-18/18 Dimethicone
[8]Iron Oxides CI 77492, Cyclopentasiloxane, Methicone, PEG/PPG-18/18 Dimethicone The example 20 and 21 compositions were then placed in a Visual Attribute Test (VAT) to compare their effectiveness at reducing the appearance of various facial attributes. As can be seen from the results of this testing, summarized in Table 16 below, increasing opacity (higher contrast ratio) by using high refractive index pigments significantly reduced the optical benefit provided by the elastomer powder and silicone oil combination in these products. Thus, this data clearly demonstrates the negative impact that increased opacity has on the optical benefits of the powder and oil systems.

TABLE 16

|  | Example 20 0% Pigment Contrast Ratio = 4.3 | Example 21 3.43% Pigment Contrast Ratio = 34 |
|---|---|---|
| Cheek Fine Lines | 0.64 | 0.03 |
| Bumpy Surface | 0.65 | −0.03 |

Examples 22-26

Mixed Particle Systems

The following examples illustrate finisher compositions according to the present disclosure. The composition of Examples 22-26 include both spherical starch particles and spherical silicone elastomer particles. The compositions in these examples are prepared by first combining the water phase ingredients in a container and mixing until uniform. The thickener is added and the water phase is mixed until uniform, and then the pH adjuster, if present, is added and the water phase is again mixed until uniform. The oil phase ingredients are combined in a separate container and mixed until uniform. The powders are next added to the oil phase and the combination is mixed until uniform. Finally, the oil/powder phase is added to the water phase and the resulting emulsion is subjected to high shear mixing (e.g., Flacktek Speedmixer, or rotor-stator mill) Table 17 shows the ingredients used to make Examples 22-26.

TABLE 17

|  | Example 22 | Example 23 | Example 24 | Example 25 | Example 26 |
|---|---|---|---|---|---|
| Water Phase: | | | | | |
| Water | 48.86 | 51.36 | 53.16 | 52.56 | 50.85 |
| Disodium EDTA | 0.05 | 0.05 | 0.05 | 0.05 | 0.05 |
| Methylparaben | — | — | — | 0.1 | — |
| Symdiol 68[1] | 0.7 | 0.7 | 0.7 | — | — |
| Glycacil L[2] | 0.09 | 0.09 | 0.09 | 0.09 | — |
| Phenoxyethanol | — | — | 0.2 | 0.5 | — |
| Glydant Plus Liquid[3] | — | — | — | — | 0.3 |
| pH Adjustor: | | | | | |
| Triethanolamine | — | — | — | 0.2 | — |
| Thickener: | | | | | |
| Sepigel 305[4] | — | — | 0.5 | 1.0 | — |
| Simulgel INS-100[5] | 2.0 | 1.5 | 1.0 | — | — |
| Makimousse-12[6] | — | — | — | — | 0.4 |
| Ultrez 10[7] | — | — | — | 0.1 | — |
| Ultrez 21[8] | — | — | — | 0.1 | — |
| Xanthan gum | — | — | — | — | 0.1 |
| Oil Phase: | | | | | |
| Cyclomethicone D5 | 11.0 | 16.0 | — | 15.0 | 14.0 |
| Dimethicone 2 cst | — | — | 12.0 | — | — |
| Dimethicone 20 cst | — | — | 3.0 | — | — |
| Dimethicone 50 cst | 11.0 | 10.0 | — | 10.0 | 8.0 |
| Dimethicone 350 cst | — | — | 3.0 | — | — |

TABLE 17-continued

|  | Example 22 | Example 23 | Example 24 | Example 25 | Example 26 |
|---|---|---|---|---|---|
| DE-23[9] | — | — | 3.0 | — | — |
| DC 5562[10] | — | — | — | — | 2.0 |
| DC1503[11] | — | — | — | — | 2.0 |
| DC9045[12] | 4.0 | — | — | — | — |
| Laureth-4 | 0.3 | 0.3 | 0.3 | 0.3 | 0.3 |
| Particles: | | | | | |
| DryFlo TS[13] | 12.0 | 10.0 | 6.0 | — | — |
| Tapioca Pure[14] | — | — | 6.0 | 10.0 | — |
| Dry Flo Pure[15] | — | — | — | — | 12.0 |
| KSP 100[16] | — | 10.0 | — | — | 5.0 |
| KSP 101[17] | 10.0 | — | — | — | — |
| KSP 102[18] | — | — | 4.0 | — | — |
| KSP 103[19] | — | — | — | 10.0 | — |
| KSP 105[20] | — | — | 4.0 | — | 5.0 |
| DC9506[21] | — | — | 3.0 | — | — |
| Total: | 100% | 100% | 100% | 100% | 100% |

[1] 1,2-hexanediol and caprylyl glycol, from Symrise
[2] Iodopropynyl butylcarbamate, PEG-4 laurate, PEG-4 dilaurate, and polyethylene glycol, from Lonza
[3] DMDM Hydantoin, Butane-1,3-diol, iodopropynyl butylcarbamate, water, from Lonza
[4] Polyacrylamide, C13-14 isoparaffin, and laureth-7, from Seppic
[5] Sodium acrylate/sodium acryloyldimethyl taurate copolymer, isohexadecane, and polysorbate 60, from Seppic
[6] Sodium polyacrylate starch, from Kobo Products Inc.
[7] Carbomer, from Lubrizol
[8] Acrylates C10-/30 alkyl acrylate crosspolymer, from Lubrizol
[9] Polydiethylsiloxane, from Gelest
[10] Bis-hydroxyethoxylpropyl dimethicone, from Dow Corning
[11] Dimethicone and dimethiconol, from Dow Corning
[12] Cyclopentasiloxane and dimethicone crosspolymer, from Dow Corning
[13] Tapioca and polymethylsilsesquioxane, from Akzo Nobel
[14] Tapioca powder, from Akzo Nobel
[15] Aluminum starch octenyl succinate, from Akzo Nobel
[16] Vinyl dimethicone/methicone silsesquioxane crosspolymer, from Shin Etsu
[17] Vinyl dimethicone/methicone silsesquioxane crosspolymer, from Shin Etsu
[18] Vinyl dimethicone/methicone silsesquioxane crosspolymer, from Shin Etsu
[19] Vinyl dimethicone/methicone silsesquioxane crosspolymer, from Shin Etsu
[20] Vinyl dimethicone/methicone silsesquioxane crosspolymer, from Shin Etsu
[21] Dimethicone/Vinyl dimethicone crosspolymer, from Dow Corning The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. In particular, U.S. Provisional Application Ser. Nos. 61/927,231, 61/927,236, 61/927,244 and 61/927,255 are incorporated herein by reference in their entirety. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A finisher composition, comprising:
   a. from about 10 to 25 wt % of substantially spherical starch particles having a mean particle size of from about 5 to 30 microns;
   b. a non-volatile oil, wherein a weight ratio of non-volatile oil to starch particles is from about 1:10 to about 3:2;
   c. from about 20 to 85 wt % of water,
   wherein the composition includes less than 1 wt % of a pigment and wherein the composition has a contrast ratio of less than about 20;
      wherein the non-volatile oil is a silicone oil and has a viscosity of from about 20 to 200 centistokes.

2. The finisher composition of claim 1, wherein the ratio of non-volatile oil to starch particles is from about 1:4 to about 3:4.

3. The finisher composition of claim 1, wherein the silicone oil is dimethicone.

4. The finisher composition of claim 1, wherein the particles size is from about 8 to 25 microns.

5. The finisher composition of claim 4, wherein the particle size is from about 10 to 20 microns.

6. The finisher composition of claim 1, wherein the starch particles are present at an amount of from about 15 wt % to about 20 wt %.

7. The finisher composition of claim 1, wherein the starch Particles are hydrophobic.

8. The finisher composition of claim 1, wherein the contrast ratio is less than about 10.

9. The finisher composition of claim 8, wherein the contrast ratio is less than about 6.

10. The finisher composition of claim 1, further comprising less than 4% non-spherical particles.

11. The finisher composition of claim 1, wherein the non-volatile oil comprises at least about 90% of a non-volatile silicone.

12. The finisher composition of claim 1, further comprising a chroma value of less than about 10.

\* \* \* \* \*